(12) United States Patent
Wild

(10) Patent No.: US 7,006,650 B1
(45) Date of Patent: Feb. 28, 2006

(54) DEVICE FOR ATTENUATING SOUND ON THE HUMAN EAR

(76) Inventor: Lars Wild, Am Sackelberg 19, D-31162 Bad Salzdetfurth (DE)

(*) Notice: Subject to any disclaimer, the term of this patent is extended or adjusted under 35 U.S.C. 154(b) by 0 days.

(21) Appl. No.: 09/890,670

(22) PCT Filed: Jan. 29, 2000

(86) PCT No.: PCT/DE00/00266

§ 371 (c)(1),
(2), (4) Date: Aug. 3, 2001

(87) PCT Pub. No.: WO00/45760

PCT Pub. Date: Aug. 10, 2000

(30) Foreign Application Priority Data

Feb. 5, 1999 (DE) .............................. 299 02 617

(51) Int. Cl.
*H04R 25/00* (2006.01)

(52) U.S. Cl. .................. 381/380; 381/72; 128/848
(58) Field of Classification Search ............... 381/72, 381/380, 328, 71.1, 74; 181/134, 135; 455/351; 128/848

See application file for complete search history.

(56) References Cited

U.S. PATENT DOCUMENTS

| | | | |
|---|---|---|---|
| 4,587,965 A | 5/1986 | de Boer et al. | |
| 5,333,622 A | 8/1994 | Casali et al. | |
| 5,631,965 A * | 5/1997 | Chang et al. | .................. 381/72 |
| 5,894,455 A | 4/1999 | Sikes | |
| 6,035,047 A * | 3/2000 | Lewis | .......................... 381/72 |
| 6,148,821 A * | 11/2000 | Falco | .......................... 128/864 |
| 6,544,199 B1 * | 4/2003 | Morris | ........................ 600/590 |

FOREIGN PATENT DOCUMENTS

| | | |
|---|---|---|
| DE | 299 02 617 | 5/1999 |
| EP | 0 440 572 | 8/1991 |
| EP | 0 590 698 | 4/1994 |
| GB | 2103807 A * | 2/1983 |

* cited by examiner

*Primary Examiner*—Brian T. Pendleton
(74) *Attorney, Agent, or Firm*—Robert C. Haldiman; Husch & Eppenberger, LLC

(57) ABSTRACT

A device for attenuating sound on the human ear, especially for preventing sleep disturbances caused by noise and other sounds. The device for attenuating sound has good damping properties and also ensures that certain alarm sounds are heard in spite of the sound-attenuating measure. To this end, a radio receiver with means for converting radio signals received from a radio station into audio signals is integrated into at least one of two sound-attenuating ear plugs. The radio station is connected to at least one alarm-sounding means and/or at least one sound-receiving means in order to convert a specific alarm and/or at least one specific sound into a radio signal that can be received by a radio receiver as it occurs.

21 Claims, 1 Drawing Sheet

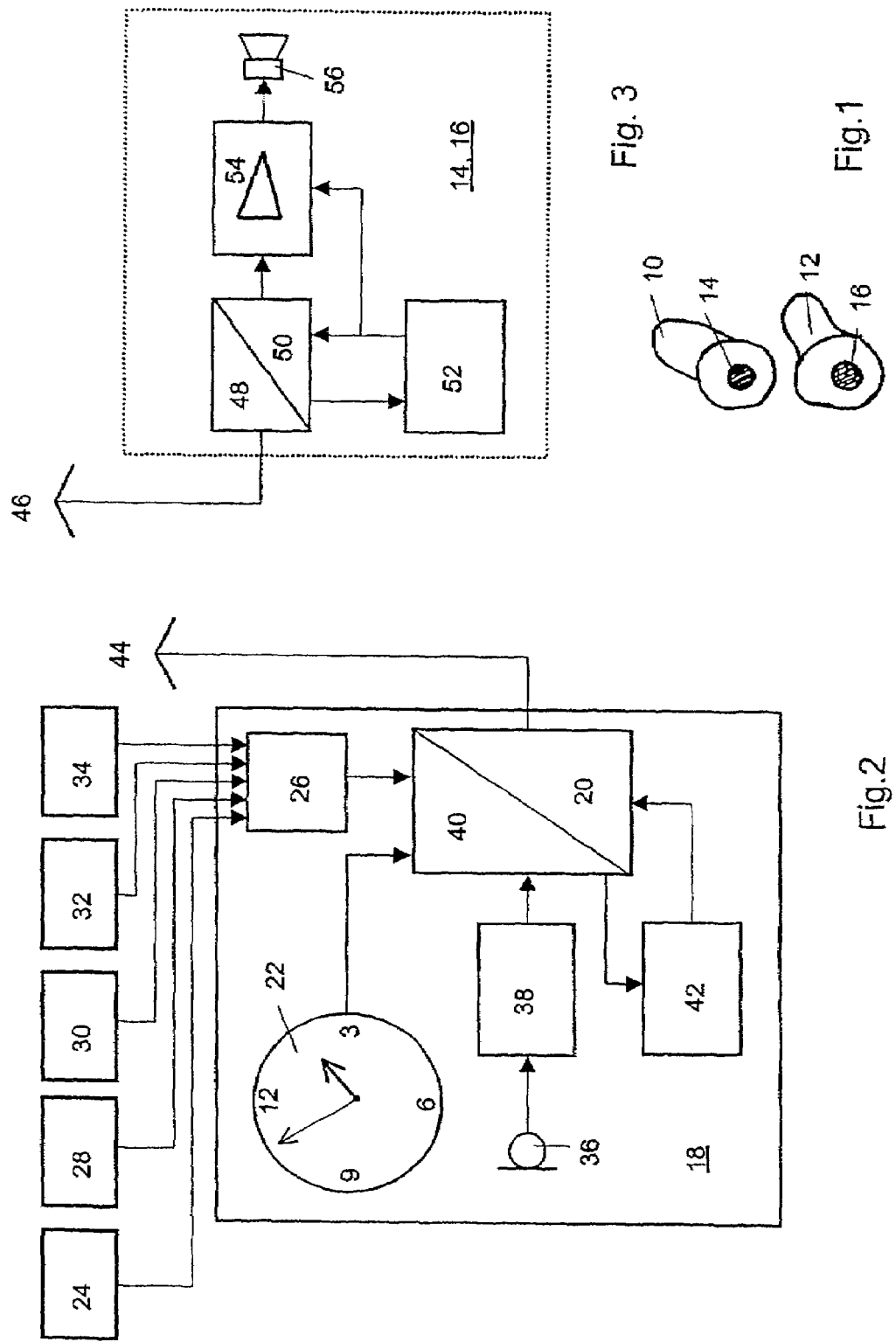

DEVICE FOR ATTENUATING SOUND ON THE HUMAN EAR

FIELD OF THE INVENTION

The invention generally concerns a device for sound insulation on the human ear and more particularly to a device for avoiding sleep disturbances due to noise and other sounds having two sound-insulating earplugs at least one of which includes an integrated radio receiver with a means for the conversion of signals received from a radio station to audio signals.

BACKGROUND OF THE INVENTION

Sleep disturbances or insomnia are an increasing and serious problem in modern times. The average sleeping time has decreased by 30 minutes in the last 20 years. Approximately one in ten persons suffer from such extreme sleep disturbances that medical assistance is necessary. The treatment of sleep disturbances is mainly in the form of sleeping tablets, which is expensive and does not guarantee success. Finally taking sleeping pills may also lead to health damage.

In most cases insomnia has a psychological cause. In particular, many people have anxious feelings leading to chronic sleep disturbances. Apart from mental and physical disorders, another major reason for the occurrence of sleep disturbances lies in external noise. This can be caused by noise outside the dwelling, for example, street noise. Secondly noise-related sleep disturbances may be due to sounds caused inside the dwelling, for example, sound reproduction equipment, children and other persons. Persistent background noise can lead to sleep disturbances even when this disturbance factor has long been eliminated.

Also snoring and impaired breathing as a result can lead to sleep disturbances of the snorer. The breathing-related sounds are caused by flapping movements of the slack soft palate or by the tongue dropping back. Frequently the occurrence of snoring sounds depends on the position of the head during sleep. Lying on one's back during sleep promotes the production of sound.

Third persons too have their sleep disturbed by snoring sounds. During snoring a volume of up to 88 decibels can be reached, which roughly corresponds to the volume of a motor truck driving directly next to the ear.

Various sound insulation means (covering the ears or capable of being inserted in them) are already known. However known means of sound insulation are disadvantageous in so far as the sound reduction obtained is not sufficient, and various important sounds such as the alarm of an alarm clock, an alarm system, a telephone or the sounds occurring in case of a break-in are not perceived.

The sound insulation means already known do in certain circumstances remedy the sound-related sleep disturbances, but are then the cause of sleep disturbances because they create anxieties. These include the fear of not hearing important sounds. In most cases, therefore, use of the sound insulation means already known is completely dispensed with.

During snoring the known sound insulation means are unsuitable for remedying the sleep disturbances of the snoring person himself or herself. In some snorers snoring is even assisted by these means, as their own snoring is no longer perceived and the snorer is no longer urged to change his or her sleeping position. Impaired breathing continues to lead to sleep disturbances.

Also the partners of snorers have very bad sleep disturbances. Use of the known sound insulation means has declined for fear of not hearing phases of breathlessness of the snoring partner and then not being able to react if breathing should cease.

BRIEF SUMMARY OF THE INVENTION

It is therefore the object of the invention to develop a device for sound insulation on the human ear or especially for avoiding sleep disturbances due to noise and other sounds. The device should on the one hand exhibits good insulation properties, for example to avoid noise-related sleep disturbances, but on the other hand prevent important sounds from being missed in spite of the sound insulation measure.

This object is achieved by a device for avoiding sleep disturbances due to noise and other sounds comprising two sound-insulating earplugs least one of which includes an integrated radio receiver, and means for converting radio signals to audio signals, means for detecting specific snoring sounds, a radio station operatively connected to the means for detecting specific snoring sounds, the radio station being operative to emit, on reception of the specific snoring sounds, a radio signal which is received by the radio receiver and converted to an audio signal.

The device makes it possible to keep any noise away from the hearing organ of the user by means of the two sound-insulating earplugs.

For the user who suffers from sleep disturbances this means that first of all one of the essential causes of sleep disturbances, namely sleep-disturbing noise, is eliminated and deep, refreshing sleep is guaranteed. For users other than those who suffer from sleep disturbances the sound-insulating earplugs can also serve to avoid nuisance caused by noise during occupational activity or in leisure time.

The device still allows the user to perceive an alarm or other sound, depending on the event, in spite of sound insulation.

"Depending on the event" means that not every conceivable alarm and/or not every sound is converted to a radio signal and transmitted from a radio station to the radio receiver, for this would impair the desired sound-insulating effect of the earplugs.

An event is therefore only a particular alarm or other sound that it is wished to perceive, which is then converted by the radio station to radio signals and transmitted to the radio receiver integrated in the earplug.

For this purpose the radio station is connected to at least one alarm-generating means and/or at least one means which picks up sounds. The radio signal received by the radio receiver is converted in the earplug to audio signals which are perceived by the user. That is to say, in spite of sound insulation the user's attention is drawn to the particular alarm and/or to the particular sound.

As a result, in the case of a user who suffers from sleep disturbances both sleep-disturbing noise and other psychologically related causes of sleep disturbances, such as the fear of not hearing important sounds, are eliminated.

Due to the device a large proportion of sleep-disturbing anxieties are reduced, so that very many people can again sleep peacefully and deeply.

In the case of users other than those who suffer from sleep disturbances, due to the device, in spite of sound insulation, their attention can be drawn to an important alarm or a sound which it is wished to perceive during occupational or leisure activity as well.

A development provides that the earplug is made of silicone or silicone-like material which is molded or foamed individually in the outer ear and in which the radio receiver with the means for conversion of the radio signals is integrally cast or foamed or fitted exchangeably.

Due to exact adaptation of the earplugs to the relevant parts of the user's ear, very good sound insulation is achieved. In particular the use of silicone or silicone-like material proved to be highly advantageous for sound insulation and for holding the radio receiver and the means for conversion of the radio signals to audio signals. Here a diaphragm as a means for conversion of the radio signals received from the radio station delivers reliable results.

Furthermore it is provided that the nature of the audio signals, in particular the volume, can be specified beforehand.

As a result, the audio signals can be adapted to the individual requirements and preferences of users.

Among the sleeping users and/or users who suffer from sleep disturbances there are for example people who sleep particularly lightly. Here there is the possibility of selecting audio signals with a relatively low volume. Moreover many users of the device have more pronounced hearing for very particular sound pitches. Here too suitable adaptations can be made.

Moreover it is conceivable that the device is used in a very sound-intensive environment. As the earplugs damp but do not completely eliminate the sounds occurring there, it is possible to select audio signals which either are very loud or differ suitably from those of the ambient sounds.

An advantageous embodiment of the invention provides that the audio signals reproduce the alarm and/or the sound identically.

This has the advantage that the user of the device can immediately associate the perceived audio signals with their origin. This is particularly important if the perceived audio signals involve an alarm which must be reacted to as quickly as possible.

Moreover it is intended that the alarm-generating means and/or means which picks up sounds is connected directly or by radio to the radio station.

As a result, alarm-generating and/or sound-producing means located both very close to the radio station and very far away from the radio station can be coupled to the radio station. Hence it is possible to pass practically any alarm or any sound which it is wished to perceive, to the user of the device.

Integration of the alarm-generating means and/or means which picks up sounds in the radio station pursues the purpose of reducing the whole device to relatively small dimensions. Advantageously, the device can thus be transported and used in any location.

A development provides that the sound-producing or alarm-generating means is a digital or analog clock with an alarm function.

Due to this development, the users of the device can have the advantage of sound insulation without having to be afraid of missing important appointments.

In the case of the sleeping persons and/or persons who suffer from sleep disturbances, the sleep disturbances caused by noise and other sounds and the psychologically caused sleep disturbances, which include the fear of missing important appointments, are remedied.

But also in the case of persons other than those who suffer from sleep disturbances, the most important reason why many people hesitate to use sound-insulating earplugs is that they are afraid of not hearing the alarm clock and missing an important appointment.

Equally, the sound-producing or alarm-generating means can be a telephone, a doorbell station, a baby monitoring device, a smoke alarm or the like device which triggers an audio alarm. Similarly it is provided that the sound-producing or alarm-generating means may be the receiving part of a movement detector.

The sound-producing or alarm-generating means which the user of the device according to the invention does not want to sleep through in spite of sound insulation, varies and depends on the user and the field of application.

By using a microphone as a means which picks up sounds it is possible to pick up both generally loud sounds and, in case of corresponding placement of the microphone, separate sounds which occur only at very particular locations. Depending on the event, corresponding sounds are then transmitted as a radio signal to the user of the device.

Events that may be wished to perceive in the case of sleeping users of the device and/or users who suffer from sleep disturbances, can be for example the sounds produced by a burglar. When normal earplugs are used, these sounds can very easily be missed.

A development provides that between the means which picks up sounds and the radio station is arranged a means for recognition of the sounds picked up and that by means of recognition only certain sounds which can be specified beforehand are transmitted from the radio station to the radio receiver.

As a result, out of a plurality of possible sounds, only certain sounds that it is wished to perceive are recorded by the user of the device.

As a means for recognition of the sounds picked up, a hardware-assisted and/or software-assisted speech and snoring recognition system is possible.

Hence it is for example possible to store very many sounds which it is wished to perceive such as speech or snoring. When the sounds picked up match the sounds stored, corresponding radio signals are transmitted to the radio receiver.

In the case of a snoring person who uses the device, snoring can be an event which leads to corresponding radio signals being transmitted to the snorer and converted to audio signals. The snorer consciously or unconsciously perceives these audio signals, and stops snoring by altering his or her sleeping position, for example.

A development provides that the audio signals are so loud that the snorer is woken up or at least urged to change his or her sleeping position.

An advantageous embodiment pursues the purpose that the device can be used by several users simultaneously, wherein each user has two sound-insulating earplugs and in at least one of the earplugs is integrated in the radio receiver with the means for the conversion of radio signals received from the radio station to audio signals.

Such a development is sensible in the case of groups of persons who spend the night, work or arrange their leisure in the same rooms or dwellings.

Moreover it is possible that, by the means for recognition of the sounds picked up, it can be specified beforehand to which user of the device a particular sound picked up is to be transmitted.

Particularly in the case of snoring persons who affect each other with their snoring sounds, the device is suitable for deliberately transmitting to the originating snorer after recognition an audio signal or his or her own original snoring sound, so that he or she stops snoring.

Preferably a miniature radio receiver is to be used as the radio receiver.

Hence particularly small embodiments of the earplugs are possible, so that the earplugs are not felt to be foreign bodies.

BRIEF DESCRIPTION OF THE DRAWINGS

Below, the invention is described with the aid of a practical example which is shown in the drawings wherein:

FIG. 1 is a schematic view of a device embodying the invention for sound insulation on the human ear, FIG. 2 is a block diagram of a radio station, and FIG. 3 is a block diagram of a miniature radio receiver.

DETAILED DESCRIPTION OF THE INVENTION

The device for sound insulation on the human ear shown in FIG. 1 includes two earplugs 10, 12 in each of which is integrated a miniature radio receiver 14, 16. Each earplug 10, 12 is made of silicone and individually adapted to the shape of the relevant parts of the ear of the respective user, as the silicone is foamed in the external ear. By this means and by the sound-insulating effect of silicone it is ensured that no disturbing sounds can be picked up by the hearing organs of the user of the device according to the invention.

The miniature radio receivers 14, 16 foamed integrally in the earplugs 10, 12 trigger, after the reception of a radio signal by means of a transducer, certain audio signals which are perceived by the hearing organs of the user.

FIG. 2 shows a block diagram of a radio station 18 with a modulator 40, an electronic switch 42, a transmitter 20, preferably for the giga-hertz range, and an aerial 44. In the radio station 18 are integrated a clock 22 with alarm function and a microphone 36. Between the microphone 36 and the modulator 40 is arranged a sound recognition system 38 that picks up sounds. Moreover, a receiving part 26 for external alarm modules is arranged in the radio station 18. Examples of external alarm modules include a movement detector 24, a telephone 28, a doorbell station 30, a baby monitoring device 32 and a smoke alarm 34 are shown and connected. A connection can also be made wirelessly by a radio, infrared or ultrasound section.

FIG. 3 shows a block diagram of the miniature radio receiver 14, 16 as arranged in the earplugs 10, 12. Each miniature radio receiver 14, 16 includes an aerial 46, a receiver 48 for the giga-hertz range with a demodulator 50, an amplifier 54, an electronic switch 52 and a sound transducer 56. The received demodulated audio signals are thus converted to audio signals after amplification by the sound transducer 56. The electronic switch 52 serves to mute the amplifier 54 when no signal is received from the radio station 18. Thus disturbing noise is suppressed.

When the device is used for sound insulation on the human ear, the miniature radio receivers 14, 16 are located within reception range of the radio station 18. If a certain wake-up time is set at the clock 22, a wake-up signal is transmitted from the radio station 18, picked up by the miniature radio receiver 14, 16 and converted by the sound transducer 56 to an audio signal which is perceived by the ear.

For a sleeping user and/or one who suffers from sleep disturbances, in this way it is possible to sleep deeply and undisturbed, that is, without any noise influence, and yet to be woken up reliably by the wake-up call of the clock 22. Also sleep disturbances caused by anxieties, for example from the fear of sleeping through an important appointment, are eliminated by this means.

The radio station 18 is further coupled to the receiving part 26 for different alarm modules. This can be a movement detector 24. In case of unauthorized opening of a door or window or movements by unauthorized persons, a signal of the movement detector 24 is picked up by the receiving part 26 and transmitted to the radio station 18. Thereupon a specific radio signal is emitted by the radio station 18 via the transmitter 20, received by the miniature radio receiver 14, 16 in the earplug 10, 12 and converted to an audio signal for the sleeping user.

Similarly, sounds which are produced by the telephone 28, the doorbell station 30, the baby monitoring device 32 or the smoke alarm 34 can also be converted to corresponding radio signals. Also sounds which are caused by a burglary of a dwelling and picked up by the microphone 36 integrated in the radio station 18 can be converted to corresponding radio signals. These radio signals are then picked up by the miniature radio receiver 14, 16 and there converted to an audio signal or wake-up signal which can be perceived by the user. An electronic switch 42 serves to switch on the transmitter 20 only when sounds or alarm are to be transmitted to the miniature radio receivers 14, 16.

The device according to the invention is further particularly well suited to the elimination of sleep disturbances caused by snoring.

By a means integrated in the radio station 18 for picking up sounds, e.g. the microphone 36, the snoring sounds of the snorer using the device are picked up. If snoring is an event which can be specified beforehand and which can be evaluated separately and identified, then a radio signal is transmitted from the radio station 18 to the miniature radio receiver 14, 16 of the snorer. The snorer perceives the corresponding audio signals. The volume of the audio signals is selected for this case such that the snorer is either woken up or urged to change his or her sleeping position and so stop snoring.

Apart from artificial sounds, the original snoring sounds can be reproduced identically as the audio signals, so that the snoring person hears his or her own snoring in a kind of sound feedback and interrupts the snoring process.

It turns out that in the case of frequent use of the device the snorer is sensitized accordingly and automatically adopts a sleeping position with no risk of snoring when he or she falls asleep.

To check whether snoring or another sound is an event, the sound recognition system 38 is arranged between the microphone 36 and the modulator 18. The sound recognition system 38 can also be integrated in the radio station 18. Due to recognition by the sound recognition system 38, only certain sounds which can be specified beforehand are transmitted from the radio station 18 to the radio receiver 14, 16.

Recognition of certain sounds can be accomplished by a hardware-assisted and/or software-assisted speech or snoring recognition system integrated in the radio station 18. The snoring sounds picked up can thus for example be associated with their originator in order to cause, on renewed snoring, the transmission of these sounds to the miniature radio receiver 14, 16 worn by the snoring person. Hence snoring is stopped early on.

In case of several users of the device, by means of the hardware-assisted and/or software-assisted speech or snoring recognition system it is of course also possible to transmit radio signals only to the user who causes snoring sounds.

Moreover, by means of the device the sleep disturbances of the partners of snorers are remedied. They decline to use the known sound insulation means for fear of missing phases of breathlessness of the snoring partner and then not being able to react in case of prolonged cessation of breathing. By means of the hardware-assisted and/or software-assisted speech or snoring recognition system it is possible to measure the periods of time between individual snoring sounds and so monitor the breathing of the snorer. In case of a life-threateningly long cessation of breathing there would then be the possibility of giving the partner of the snoring person the alarm by an audio signal.

It goes without saying that the earplugs 10, 12 can also be used by non-sleeping persons independently of the radio station 18, in order to obtain protection against noise in case of severe noise pollution during leisure time or occupational activity. In connection with the radio station 18 described above, certain signals, for example warning signals in construction work, can nevertheless be heard by the persons shielded against the effect of noise.

The invention is not confined to the practical example described above. On the contrary, numerous modifications are conceivable within the scope of the basic concept which consists of the provision of sound-insulating earplugs 10, 12 provided with the miniature radio receiver 14, 16 which can receive particular event-related signals from the radio station 18 and generate particular audio signals in the ear, the radio station 18 being connected to alarm-generating means and/or means which pick up sounds 24–34.

Target groups are, amongst others, all night-shift emergency services, prison staff, fire brigade, nurses, doctors, other care services, security services, police, disaster prevention associations, armed forces units, reserve services of all kinds or all day-shift persons who are subjected to an elevated noise level.

What is claimed is:

1. A device for avoiding sleep disturbances due to noise and other sounds, comprising
    means for detecting specific snoring sounds by capturing them through a microphone and a sound recognition system wherein a specific snoring sound is stored and compared with the captured snoring sound, in order to detect the specific snoring sound;
    a radio station operatively connected to said means for detecting specific snoring sounds and further including an input mechanism being at least one of a clock with an alarm function, a telephone, a doorbell station, a baby monitoring device, a smoke alarm, and a receiving part of a movement of a movement detector, and being operative to emit on reception of the specific snoring sound and/or an input from the input mechanism, a radio signal, and
    two sound-insulating earplugs at least one of which includes an integrated radio receiver for receiving the radio signal emitted by the radio station and means for converting received radio signals to audio signals.

2. Device according to claim 1, characterized in that the earplug (10, 12) is made of silicone or silicone-like material which is molded or foamed individually in the outer ear and in which the radio receiver (14, 16) with the means for the conversion of radio signals received from the transmitting station (18) to audio signals is integrally cast or foamed or fitted exchangeably.

3. Device according to claim 1, characterized in that the means for the conversion of radio signals received from the transmitting station (18) to audio signals is a diaphragm.

4. Device according to claim 1, characterized in that the nature of the audio signals, in particular the volume, can be adjusted beforehand.

5. Device according to claim 1, characterized in that the audio signals reproduce the alarm and/or the sound identically.

6. Device according to claim 1, characterized in that the alarm-generating means (24–34) and/or means which picks up sounds (36) is connected directly or by radio to the transmitting station (18).

7. Device according to claim 1, characterized in that the alarm-generating means (24–34) and/or means which picks up sounds (36) is integrated in the transmitting station (18).

8. Device according to any of claim 1, characterized in that the sound-producing or alarm-generating means is a digital or analogue clock (22) with an alarm function.

9. Device according to claim 1, characterized in that the sound-producing or alarm-generating means is a telephone (28), a doorbell station (30), a baby monitoring device (32), a smoke alarm (34) or the like device which triggers an audio alarm.

10. Device according to claim 1, characterized in that the sound-producing or alarm-generating means is the receiving part (26) of a movement detector (24).

11. Device according to claim 1, characterized in that the means which picks up sounds (36) is a microphone.

12. Device according to any of claim 1, characterized in that between the means which picks up sounds (36) and the transmitting station (18) is arranged a means for recognition of the sounds picked up (38) and in that by means of recognition only certain sounds which can be specified beforehand are transmitted from the transmitting station (18) to the radio receiver (14, 16).

13. Device according to claim 12, characterized in that the means for recognition of the sounds picked up (38) is a hardware-assisted and/or software-assisted speech or snoring recognition system.

14. Device according to claim 13, characterized in that the audio signals caused by the snoring and transmitted to the person snoring are of such a volume that the person snoring is wakened or at least caused to change his sleeping position.

15. Device according to claim 1, characterized in that the device can be used by several users simultaneously, wherein each user has two sound-insulating earplugs (10, 12) and in at least one of the earplugs (10, 12) is integrated a radio receiver (14, 16) with a means for the conversion of radio signals received from a transmitting station (18) to audio signals.

16. Device according to claim 15, characterized in that, by the means for recognition of the sounds picked up (38), it can be specified beforehand to which user of the device a particular sound picked up is to be transmitted.

17. Device according to claim 1, characterized in that the radio receiver (14, 16) is a miniature radio receiver.

18. The device according to claim 3, wherein in that the input mechanism is connected by radio to the radio station.

19. The device according to claim 14, characterized in that the means for recognizing sounds is a software-assisted sound recognition system.

20. The device according to claim 3, wherein the input mechanism includes means for generating an alarm.

21. The device according to claim 3, wherein the input mechanism includes means for picking up further specific sounds.

* * * * *